United States Patent [19]

Kollmeier et al.

[11] Patent Number: 4,654,161
[45] Date of Patent: Mar. 31, 1987

[54] SILOXANES WITH BETAINE GROUPS, THEIR SYNTHESIS AND USE IN COSMETIC PREPARATIONS

[75] Inventors: Hans-Joachim Kollmeier, Essen; Rolf-Dieter Langenhagen, Hattingen-Niederwenigern; Klaus Hoffmann, Essen, all of Fed. Rep. of Germany

[73] Assignee: Th. Goldschmidt AG, Essen, Fed. Rep. of Germany

[21] Appl. No.: 731,501

[22] Filed: May 7, 1985

[30] Foreign Application Priority Data

May 15, 1984 [DE] Fed. Rep. of Germany ....... 3417912

[51] Int. Cl.[4] ............................................. C11D 17/00
[52] U.S. Cl. ................................. 252/174.15; 252/546; 252/DIG. 14; 424/70; 528/26; 528/28; 528/33; 528/41; 556/413; 556/420; 556/437; 556/467
[58] Field of Search ................. 424/70; 252/DIG. 14, 252/546, 174.15; 556/413, 420, 437, 467; 528/28, 26, 33, 41

[56] References Cited

U.S. PATENT DOCUMENTS 4,185,087  1/1980  Morlino ...................... 252/DIG. 13
4,283,191  8/1981  Koerner et al. ...................... 252/8.9
4,490,356 12/1984  Sebag et al. ............................ 424/70

Primary Examiner—Melvyn I. Marquis
Attorney, Agent, or Firm—Toren, McGeady and Goldberg

[57] ABSTRACT

Organopolysiloxanes that have betaine groups and are of the general formula

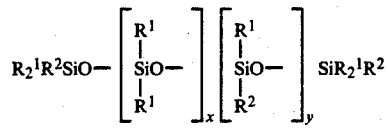

in which
$R^1$ can represent the same or different groups in the molecule and may be an alkyl radical with 1 to 18 carbon atoms, an aryl radical or a polyoxyalkylene radical with the proviso that at least 70% of the $R^1$ radicals are methyl radicals,
$R^2$ may be the same as $R^1$, with the proviso that at least one $R^2$ radical represents the

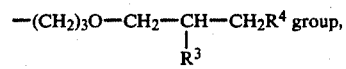

in which $R^3$ and $R^4$ are different, one radical representing a hydroxyl group, and the other the

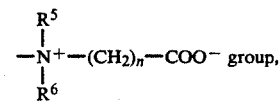

in which $R^5$ and $R^6$ are the same or different and represent an alkyl radical with 1 to 4 carbon atoms or a benzyl radical, and n=1, 2, or 3,
x has a value of 0 to 200, and
y has a value of 1 to 50, as well as processes for their synthesis and their use in cosmetic preparations.

19 Claims, No Drawings

SILOXANES WITH BETAINE GROUPS, THEIR SYNTHESIS AND USE IN COSMETIC PREPARATIONS

BACKGROUND OF THE INVENTION

1. Field of the Invention

The invention relates to novel organopolysiloxanes with betaine groups and to processes for the synthesis of these compounds. It also relates to the use of these compounds in cosmetic preparations.

2. Description of the Prior Art

The use of organopolysiloxanes for the preparation of hair care products is well known. However, in "Chemie und Technologie der Silicone" (Chemistry and Technology of the Silicones) by Water Noll, Chemie Publishing House, 2nd edition, 1968, page 536, it is stated that normal polydimethylsiloxanols are unable to maintain the hairdo independently of the effects of moisture. Rather, the silicone would have to be fixed on the hair with the help of functional groups.

German Auslegeschrift No. 14 93 384 discloses organosiloxane compounds or mixtures of compounds of the formula:

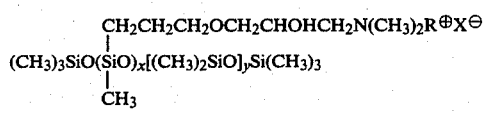

in which R represents hydrogen or $CH_3$, X represents halogen, x=1 to 10, and y=0 to 8.5, and the ratio of y:x is not greater than 8.5:1.

These organosiloxanes with quaternary ammonium groups can be synthesized by reacting an epoxysiloxane compound having the formula

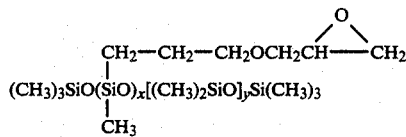

in a known manner with dimethylamine, and converting the dimethylamino organosiloxane compound obtained which has the formula

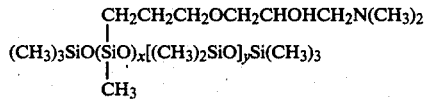

in a known manner with a hydrogen halide or with a methyl halide into the quaternary ammonium compound of the aforementioned formula.

According to U.S. Pat. No. 4,185,087, the aforementioned organopolysiloxanes with quaternary ammonium groups can be used for hair care products. As disclosed therein, simple aqueous shampoos may release soil from hair and remove an excess of grease. With most shampoos, however, degreasing of the hair would be carried out so thoroughly that damage to the hair could be observed. After washing, the hair becomes electrostatically charged and therefore difficult to comb. While the addition of lanolin derivatives, glycol, fatty esters or proteins improves the ability to handle the hair after washing, it does interfere with foaming. The hair would become somewhat sticky and feel unnatural. According to U.S. Pat. No. 4,185,087, the specific organopolysiloxanes with the quaternary ammonium groups should eliminate these disadvantages and improve the combability of the washed hair, give better hold to the hair set, and improve the gloss.

Similar teachings are contained in European Pat. Nos. 0 017 121 and 0 017 122 which describe organopolysiloxanes with quaternary ammonium groups for use in shampoos and hair conditioners to improve the combing properties of the hair. The compounds correspond to the general formula:

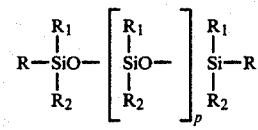

in which $R_1$ and $R_2$ represent an alkyl radical with 1 to 4 carbon atoms or an aryl radical, p represents the numbers 0 to 50, and R the radicals:

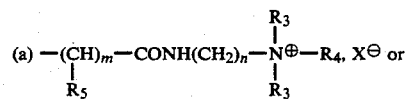

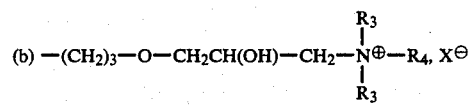

in which $R_3$ represents an alkyl or hydroxyalkyl radical with 1 to 3 carbon atoms, $R_4$ represents a radical identical with $R_3$, aryl—$CH_2$—, or the allyl radical, $R_5$ represents hydrogen or the methyl radical, $X^\ominus$ represents the anions $Cl^\ominus$, $Br^\ominus$, $I^\ominus$, $CH_3SO_4^\ominus$ or $C_2H_5SO_4^\ominus$ and m the numbers 2 to 10 and n the numbers 2 to 4.

Finally, published European Patent Application No. 0095 238 discloses a composition which essentially comprises the following components:

(A) a siloxane of the general formula

in which R is only described functionally as a group which brings about adhesion to the hair, for example, an amino, carboxyl or quaternary ammonium group, X is a hydrogen radical or a phenyl, hydroxyl or saturated hydrocarbon group with 1 to 8 carbon atoms, a has a value of 0 to 3, b has a value of 0 to 1 and n+m has a value of 1 to 1999, n having a value from 0 to 2000 and m a value of 1 to 2000;

(B) a surfactant;

(C) an additive for improving the freeze/thaw stability, and (D) water.

It therefore follows from the state of the art that organopolysiloxanes with quaternary ammonium groups have a strong substantivity on hair and endow it with good combability and gloss. However, their poor compatibility with anionic components, especially with anionic surfactants, is a disadvantage in hair care preparations. Moreover, they may also lead to irritation of the skin, especially of the mucous membrane, and to irritation of the eye which is extremely undesirable, especially in shampoos.

SUMMARY OF THE INVENTION

We have discovered additives for hair cosmetics which have the good properties of the organopolysiloxanes with quaternary ammonium groups, but are compatible with anionic additives, especially with anionic surfactants. At the same time, the inventive siloxane derivatives are less irritating to the skin than prior art compounds.

More particularly, the compounds having these properties are organopolysiloxanes which have one or more betaine groups. The object of the invention therefore are compounds having the general formula

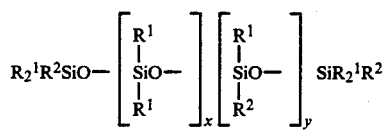

in which
$R^1$ can represent the same or different groups in the molecule and may be an alkyl radical with 1 to 18 carbon atoms, an aryl radical or a polyoxyalkylene radical with the proviso that at least 70% of the $R^1$ radicals are methyl radicals, $R^2$ may be the same as $R^1$, with the proviso that at least one $R^2$ radical represents the

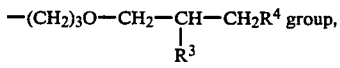

in which $R^3$ and $R^4$ are different, one radical representing a hydroxyl group, and the other the

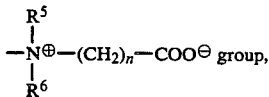

in which $R^5$ and $R^6$ are the same or different and represent an alkyl radical with 1 to 4 carbon atoms or a benzyl radical, and n=1, 2, or 3,
x has a value of 0 to 200, and
y has a value of 1 to 50.

It is evident from the general formula I that the betaine group(s) may be linked terminally or laterally.

At least 70% of the $R^1$ radicals are methyl radicals. Especially preferred are those polysiloxanes in which all the $R^1$ radicals are methyl radicals. Up to 30% of the $R^1$ radicals may be alkyl radicals, with 2 or more and, preferably, with 12 to 18 carbon atoms, or aryl radicals. Examples of such alkyl radicals are the ethyl, propyl, isopropyl, butyl, hexyl, isooctyl, decyl, dodecyl or stearyl radicals. The aryl radical generally is a phenyl radical. The alkyl radicals as well as the aryl radicals may be substituted.

It is also possible that up to 30% of the $R^1$ radicals are polyoxyalkylene radicals and especially those having the general formula:

$$-(CH_2)_3O(C_mH_{2m}O)_pQ$$

in which the $-(C_mH_{2m}O)_p$ group is built up from ethylene oxide and propylene oxide and m has an average value of 2.0 to 2.6, p has a value of 1 to 25, and Q is a hydrogen or alkyl radical with 1 to 4 carbon atoms. Compounds are preferred in which 3 to 10% of the $R^1$ radicals are polyoxyalkylene radicals.

At least one $R^2$ radical must represent the

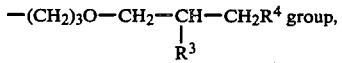

in which one of the $R^3$ and $R^4$ radicals is a hydroxyl radical. The other radical is the

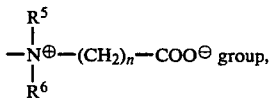

in which $R^5$ and $R^6$ preferably are methyl radicals. They may, however, also be ethyl, propyl, isopropyl or butyl radicals or a benzyl radical. In this formula, n has a value of 1, 2 or 3, with n=1 being preferred.

The value of x preferably is 2 to 100, and especially, 5 to 50, while the value of y is 1 to 25, and especially, 2 to 10.

Examples of inventive organopolysiloxanes with betaine groups are:

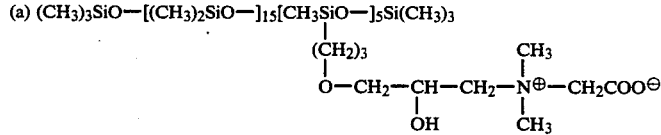

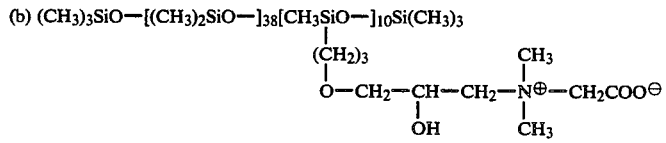

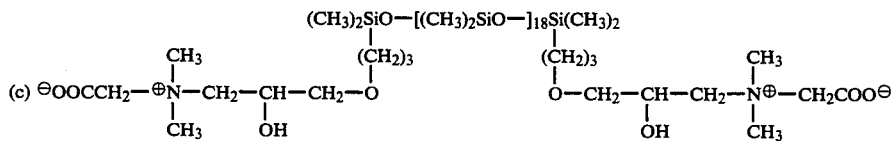

-continued (d) $(CH_3)_3SiO-[(CH_3)_2SiO-]_{15}[CH_3SiO-]_3[CH_3SiO-]_5Si(CH_3)_3$
with side chains:
$(CH_2)_{15}$, $(CH_2)_3$, and $-CH_2-CH(OH)-CH_2-N^{\oplus}(CH_3)_2-CH_2COO^{\ominus}$
where $(CH_2)_{15}$ bears $CH_3$ and $(CH_2)_3$ bears $O-CH_2-CH(OH)-CH_2-N^{\oplus}(CH_3)_2-CH_2COO^{\ominus}$ and (e) $(CH_3)_3SiO-[(CH_3)_2SiO-]_{13}[CH_3SiO-]_{2.5}[CH_3SiO-]_{2.5}Si(CH_3)_3$
with side chains $(CH_2)_3$ bearing $H-(OC_3H_6-)_3(OC_2H_4-)_{13}O$, and $(CH_2)_3$ bearing $O-CH_2-CH(OH)-CH_2-N^{\oplus}(CH_3)_2-CH_2COO^{\ominus}$.

The inventive compounds generally are viscous to highly viscous, oily to pasty, and colorless to yellow products. The solubility of the inventive compounds is essentially determined by the ratio of the number of betaine groups to the number of siloxy units $(R_2^1SiO)$ as well as by the nature of the $R^1$ radicals. Higher betaine group contents and/or the presence of polyoxyalkylene radicals with a predominant proportion of oxyethylene units results in products, which are soluble in water and lower alcohols or glycols. On the other hand, oil compatible or oil dispersible products can be obtained by incorporating alkyl radicals with 12 to 18 carbon atoms. Products which are soluble in water or glycols, are generally preferred for use in hair care products.

We also have discovered an inventive method for the synthesis of the inventive compounds. In this process, compounds of the general formula (a) $R_2^1R^7SiO-\left[\begin{array}{c}R^1\\|\\SiO-\\|\\R^1\end{array}\right]_x\left[\begin{array}{c}R^1\\|\\SiO-\\|\\R^7\end{array}\right]_y SiR_2^1R^7$  II in which $R^7$ may be the same as $R^1$ with the proviso that at least one of the $R^7$ radicals is the $-(CH_2)_3O-CH_2-CH\overset{\diagdown}{\underset{O}{\diagup}}CH_2$ group, are reacted in a known manner with, based on the $-(CH_2)_3O-CH_2-CH\overset{\diagdown}{\underset{O}{\diagup}}CH_2$ group, equimolar amounts of compounds of the general formula $\begin{array}{c}R^5\\|\\N-(CH_2)_nCOOH,\\|\\R^6\end{array}$ or (b) $R_2^1R^8SiO-\left[\begin{array}{c}R^1\\|\\SiO-\\|\\R^1\end{array}\right]_x\left[\begin{array}{c}R^1\\|\\SiO-\\|\\R^8\end{array}\right]_y SiR_2^1R^8$  III in which $R^8$ may be the same as $R^1$, with the proviso that at least one of the $R^8$ radicals is the $-(CH_2)_3O-CH_2-CH(R^3)-CH_2R^9$ group, in which $R^3$ and $R^9$ are different, one being a hydroxyl radical and the other the $\begin{array}{c}|\\R^5-N-R^6\end{array}$ group, are reacted in a known manner with, based on the $\begin{array}{c}|\\R^5-N-R^6\end{array}$ group, equimolar amounts of compounds of the general formula $X-(CH_2)_n-COOY$ in which X is a chlorine or bromine radical and
Y is an alkali radical.

Those skilled in the art are familiar with the synthesis of compounds of Formulas II and III, which serve as starting compounds in the inventive process, and this synthesis is not an object of this invention. For example, the appropriate allyl compounds, e.g., $CH_2=CH-CH_2OCH_2CH\overset{\diagdown}{\underset{O}{\diagup}}CH_2$ can be added to hydrogen siloxanes corresponding to Formula II, in which, however, the $R^7$ radicals are hydrogen radicals, and, for synthesizing compounds III, these initially obtained addition products can be reacted with amines of the formula $HNR^5R^6$.

The reaction of compounds of the general Formula II with compounds of the general formula $\begin{array}{c}R^5\\|\\N-(CH_2)_nCOOH\\|\\R^6\end{array}$ or the reaction of compounds of the general Formula III with compounds of the general formula $X-(CH_2-$ $)_n$—COOY is, in each case, carried out by known methods. Preferably, the reaction is conducted at elevated temperatures, especially at temperatures ranging from 40° to 160° C. The reaction can also be carried out in the presence of solvents, in which case the upper temperature limit is determined by the boiling point of the solvent used. Examples of suitable solvents are water, lower alcohols or glycols.

The inventive compounds exhibit the desired combination of properties. They are compared in the following table with similar products used according to the state of the art.

TABLE

| Additive | Substantivity on Hair | Combability and Gloss of Hair | Skin Irritation | Compatibility with Anionic Additives |
|---|---|---|---|---|
| Siloxane with polyether groups | weak | weak | none | good |
| Siloxane with anionic groups | none | none | weak | good |
| Siloxane with amino groups | average | average | average | good |
| Siloxane with quaternary amino groups | strong | good | weak | poor |
| Siloxane with betaine groups | average | good | none | good |
| Siloxane-free betaine | average | weak | none | good |

It can be seen from the table that the organopolysiloxanes with betaine groups have the desired combination of properties, which is not exhibited by any of the other compounds.

It is therefore a further object of the invention to use the inventive compounds in cosmetic preparations, especially in preparations for the care of hair. In this connection, hair cosmetics can be shampoos or hair conditioner, depending on whether the emphasis is on the cleansing effect or on the care effect and the effect of better combability. Shampoos to which the inventive organopolysiloxane with betaine groups have been added in amounts of 0.1 to 10 weight percent, and which contain up to 30 weight percent of substances with detergent activity, besides water and possibly other additives, cause the washed hair to have fullness and an agreeable handle, to show the desired gloss and to be easily combable. Practically no electrostatic charging of the hair is to be observed. In hair care products, such as, hair tonics or hair sprays, the inventive compounds in amounts of 0.1 to 5% already bring about a significant improvement in combability of the hair and develop fullness and gloss.

Conventional additives, such as, solvents, thickeners, perfumes, preservatives, complexing agents, foam stabilizers, opacifiers, luster developing agents or other conventional additives, such as, dyes, may be added to the hair care products. Examples of formulations are:

| Material for a Cream-Treatment Rinse | |
|---|---|
| Cetyl alcohol | 6 parts by weight |
| TEGINACID ® H (mixture of glycerin monostearate and glycerin distearate with polyglycol fatty alcohol ethers, a commercial product of Th. Goldschmidt AG) | 6 parts by weight |
| Glycerin | 3 parts by weight |
| Betaine siloxane (Example 1) | 1 part by weight |
| Water | 84 parts by weight |

| Conditioning Shampoo | |
|---|---|
| (a) Sodium lauryl ether sulfate | 3 parts by weight |
| Ammonium alkyl ether sulfate | 6 parts by weight |
| TAGAT ® KL 141 (a polyoxyethylene-propylene glycol dioleate, a commercial product of Th. Goldschmidt AG) | 5 parts by weight |
| Betaine siloxane (Example 1) | 2 parts by weight |
| Water | 84 parts by weight |
| (b) Coconut fatty acid diethanolamide | 0.5 parts by weight |
| Sodium lauryl ether sulfate | 30 parts by weight |
| Salt | 1.5 parts by weight |
| TEGO ®-Betaine L 7 (alkyl-amidobetaine), a commercial product of Th. Goldschmidt AG | 8 parts by weight |
| Betaine siloxane (Example 1) | 2 parts by weight |
| Water | 58 parts by weight. |

The inventive compounds may also be added to skin care products. As a component of soap or skin creams, they form a fine, non-irritating, non-greasy film on the skin. In contrast to dimethylsiloxanes of low viscosity, especially the cyclic dimethylsiloxanes, they do not evaporate on the skin and therefore provide a constant protection.

A liquid soap may moreover have the following composition:

| | |
|---|---|
| TAGAT ® 0 2 (polyoxyethylene ether of the oleic acid monoester of glycerin, a commercial product of Th. Goldschmidt AG) | 1 part by weight |
| Coconut fatty acid diethanolamide | 0.5 parts by weight |
| Sodium lauryl ether sulfate | 30 parts by weight |
| TEGO ®-betaine L 7 (alkylamido-betaine), a commercial product of Th. Goldschmidt AG | 7 parts by weight |
| Salt | 2 parts by weight |
| Betaine siloxane (Example 2) | 2 parts by weight |
| Water | 57.5 parts by weight |

The inventive process is explained in greater detail in the following examples. Furthermore, application-related tests are shown for comparison with products of the state of the art.

EXAMPLE 1

In an autoclave, 214.6 g (=0.1 mole) of a siloxane having the average formula

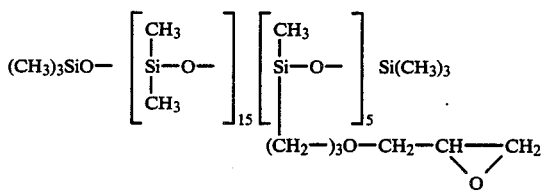

and 110 g (approximately 100% excess) of a 40% aqueous dimethylamine solution, are reacted for 3 hours at 120° C. with stirring. At the same time, the pressure increases to about 4.5 bar. The yellow, two-phase reaction mixture obtained is freed from water and excess amine by distillation (bath temperature: up to 90° C., pressure: 20 mbar). The brown, liquid residue obtained is slightly cloudy and is filtered. A clear product is obtained with a nitrogen content of 2.85% (theoretical: 2.95%).

The previously synthesized siloxane that contains tertiary amine groups (172 g=0.35 moles of amino groups) is stirred for 5 hours at 100° C. with 40.8 g (=0.35 moles) of ClCH₂COONa in 230 g of water in a 3-neck flask equipped with thermometer, stirrer and reflux condenser. The initially cloudy formulation becomes clear after about 1 hour. At the end of the reaction, 2.75% of ionic chlorine can be determined in the solution. This value corresponds to a 98.2% conversion. The water is subsequently distilled off in a rotary evaporator (bath temperature: 90° C., pressure: 20 mbar). A cloudy residue remains, which is still capable of flowing at 90° C., but is almost solid at room temperature. In order to remove the sodium chloride formed, the residue is taken up in 150 ml of i-propanol and filtered. The solution is subsequently concentrated once again in a rotary evaporator. A clear, light brown product is obtained, which is barely able to flow at room temperature. Analysis reveals a betaine nitrogen content of 2.4% (theoretical: 2.55%).

The substance is dissolved in water to form a 1% and a 0.1% solution and the surface tensions are measured at 20° C.

1% solution: 28.1 mN/m
0.1% solution: 29.0 mN/m

EXAMPLE 2

A 30% ethanolic solution of dimethylamine (140 g) is added at 20° C. to a flask equipped with thermometer, stirrer and reflux condenser. Over a period of 30 minutes, 236.2 g (=0.05 moles) of a siloxane having the average composition

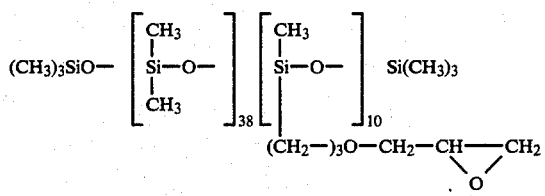

are added dropwise to this solution. At the same time, the temperature rises to about 40° C. After 1 hour, the solution is heated to the refluxing temperature and stirred for a further 5 hours. The clear, yellowish solution is freed from excess amine and from ethanol in a rotary evaporator (bath temperature: 80° C., pressure 22 mbar). A clear, yellow, slightly viscous liquid is obtained as residue, the nitrogen content of which is 2.7% (theoretical: 2.71%).

The siloxane obtained (207.5 g=0.4 moles of amino groups), which contains tertiary amino groups, together with 46.6 g (0.4 moles) of ClCH₂COONa in 207.3 g of water and 307.6 g of 1,2-propylene glycol are added to a 3-neck flask equipped with thermometer, reflux condenser, and stirrer and stirred for 5 hours at 100° C. After about 1 hour, the formulation becomes clear. At the end of the reaction, 1.8% of ionic chloride may be determined in the clear, yellow, slightly viscous solution. This value corresponds to a 97.8% conversion. In addition, the analysis reveals that the solution contains 0.7% betaine nitrogen (theoretical: 0.73%).

The solution obtained consists of 30% of the desired siloxane that contains betaine groups, 3% of sodium chloride, 27% of water, and 40% of 1,2-propylene glycol.

By diluting with water, 1 and 0.1% solutions are prepared, whose surface tensions are determined (at 20° C.):

1% solution: 25.5 mN/m
0.1% solution: 26.5 mN/m.

EXAMPLE 3

A 33% ethanolic solution of dimethylamine (70 g) is added at room temperature to a flask equipped with thermometer, stirrer and reflux condenser. Over a period of 25 minutes, 372.2 g (=0.1 moles) of a siloxane having the average composition

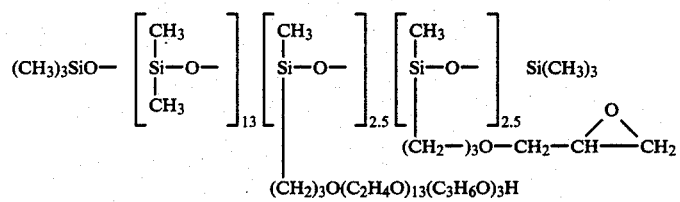

are added dropwise to this solution. This siloxane which has polyoxyalkylene radicals in addition to epoxy groups, can be synthesized according to known procedures by the addition, in the presence of platinum catalysts, of

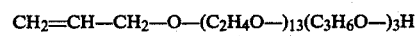

CH₂=CH—CH₂—O—(C₂H₄O—)₁₃(C₃H₆O—)₃H and allyl glycidyl ether to the appropriate siloxane

(CH₃)₃SiO[(CH₃)₂SiO]₁₃[(CH₃)HSiO]₅Si(CH₃)₃ that carries SiH groups.

After the addition of the siloxane to the dimethylamine solution, the temperature is raised to 75° C. and stirring is continued for 6 hours. Subsequently, the excess amine and the ethanol are distilled off in a rotary evaporator (bath temperature: 80° C., pressure: 15 mbar). A clear yellow, viscous product with a nitrogen content of 0.87% (theoretical: 0.91%) is obtained.

The product obtained (322 g=0.2 moles of amino groups), together with 23.3 g (=0.2 moles) of ClCH₂COONa in 321.9 g of water and 166.8 g of 1,2-propylene glycol is added to a 3-neck flask equipped with thermometer, stirrer and reflux condenser and stirred for 6 hours at 100° C. The formulation becomes clear after about 15 minutes. At the end of the reaction, 0.8% ionic chlorine can be detected in the clear, yellow solution. This corresponds to a 94.1% conversion. In addition, the analysis reveals a betaine nitrogen content of 0.31% (theoretical: 0.34%).

The solution obtained consists of 40% of a siloxane modified with betaine groups and polyoxyalkylene radicals, 1.4% of sodium chloride, 38.6% of water, 20% of 1,2-propylene glycol.

By diluting with water, 1% and 0.1% solutions are prepared for surface tension measurements (at 20° C.). The following values are obtained:

1% solution: 25.7 mN/m
0.1% solution: 26.4 mN/m

EXAMPLE 4

Testing the Inventive Compounds in Hair Care Products A conditioning shampoo of the following composition:

| | |
|---|---|
| Sodium laurylether sulfate | 3 parts by weight |
| Ammonium alkylether sulfate | 6 parts by weight |
| TAGAT ® KL 141 (monoleic acid ester of the polyoxyethylen ether of propylene glycol, a commercial product of Th. Goldschmidt AG) | 5 parts by weight |
| Betaine siloxane (Example 1) | 2 parts by weight |
| Water | 84 parts by weight | is compared in respect to its action with a shampoo formulation in which the inventive betaine siloxane is replaced by a cationic organosiloxane compound as described in German Auslegeschrift No. 14 93 384, wherein x=15, y=5 and X=Cl$^\ominus$.

The preparation with the betaine siloxane is clear, while the cationic siloxane leads to cloudiness.

The half-side comparison of the practical application on human hair resulted in the following evaluation:

With respect to foaming, the creaminess of the foam, the dry combability, the anti-electrostatic effect and the fullness of the hair, the inventive betaine siloxane is superior. The cationic siloxane gives a somewhat better result only with respect to the wet combability. This is, however, associated with a heavier loading and therefore a lesser fullness of the hair.

We claim:

1. Compounds having the formula

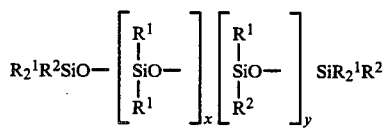

in which
R$^1$ is identical or different groups in the molecule and is an alkyl radical with 1 to 18 carbon atoms, an aryl radical or a polyoxyalkylene radical with the proviso that at least 70% of the R$^1$ radicals are methyl radicals,
R$^2$ is the same as R$^1$, or an ether group having the formula

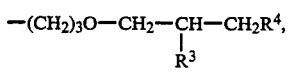

in which R$^3$ and R$^4$ are different, one of the R$^3$ or R$^4$ being a hydroxyl group, and the other the

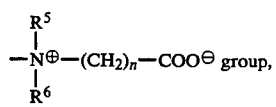

in which R$^5$ and R$^6$ are the same or different and represent an alkyl radical with 1 to 4 carbon atoms or a benzyl radical, and n=1, 2, or 3, with the proviso that at least one R$^2$ radical is said ether group,
x has a value of 0 to 200, and
y has a value of 1 to 50.

2. The compound of claim 1 wherein all of the R$^1$ radicals are methyl.

3. The compound of claim 1 wherein up to 30% of the R$^1$ radicals are alkyl groups having from 12 to 18 carbon atoms, or aryl radicals.

4. The compound of claim 3 wherein the alkyl radical is selected from the group consisting of ethyl, propyl, isopropyl, butyl, hexyl, isooctyl, decyl, dodecyl and stearyl.

5. The compound of claim 3 wherein the aryl radical is phenyl.

6. The compounds of claim 1 wherein up to 30% of the R$^1$ radicals are polyoxyalkylene radicals having the formula

wherein m has an average value of 2.0 to 2.6,
p has a value of 1 to 25, and
Q is a hydrogen or alkyl radical with 1 to 4 carbon atoms.

7. The compound of claim 6 wherein 3 to 10% of the R$^1$ radicals are polyoxyalkylene radicals.

8. The compound of claim 1 wherein R$^5$ and R$^6$ are methyl radicals.

9. The compound of claim 1 wherein R$^5$ and R$^6$ are selected from the group consisting of ethyl, propyl, isopropyl, and butyl.

10. The compound of claim 1, 2, 3, 4, 5, 6, 7, 8, or 9 wherein n is 1.

11. The compound of claim 1, 2, 3, 4, 5, 6, 7, 8, or 9 wherein x is 2 to 100, and y is 1 to 25.

12. The compound of claim 11, wherein x is 5 to 50 and y is 2 to 10.

13. A process for the synthesis of compounds of claim 1 comprising reacting compounds having the formula

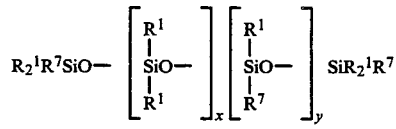

in which R$^7$ may be the same as R$^1$, with the proviso that at least one of the R$^7$ radicals is the

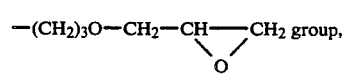

with equimolar amounts of compounds having the formula

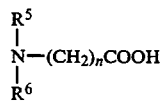

based on the

—(CH$_2$)$_3$O—CH$_2$—CH—CH$_2$ group.
       \O/

14. A process for the synthesis of compounds of claim 1 comprising reacting compounds having the formula

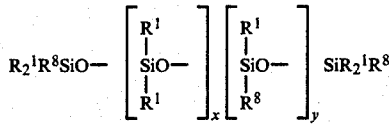

in which R$^8$ is the same as R$^1$, with the proviso that at least one of the R$^8$ radicals is the —(CH$_2$)$_3$O—CH$_2$—CH—CH$_2$R$^9$
                    |
                    R$^3$ group, in which R$^3$ and R$^9$ are different, one being a hydroxyl radical and the other the

R$^5$—N—R$^6$,
    | with equimolar amounts of compounds having the formula X—(CH$_2$)$_n$—COOY, in which X is a chlorine or bromine radical and Y is an alkali radical, based on the

R$^5$—N—R$^6$
    | group.

15. The process of claim 13 or 14 wherein the reaction is carried out in a solvent at a temperature of 40° C. or up to the boiling point of the solvent used.

16. The process of claim 15 wherein the temperature is from 40° C. to 160° C.

17. A cosmetic preparation for the care of the hair containing an effective amount of the compound of claim 1, 2, 3, 4, 5, 6, 7, 8 or 9.

18. A shampoo containing an effective amount of the compound of claim 1, 2, 3, 4, 5, 6, 7, 8 or 9.

19. A hair conditioner containing an effective amount of the compound of claim 1, 2, 3, 4, 5, 6, 7, 8 or 9.

* * * * *